(12) United States Patent
Carr

(10) Patent No.: US 10,690,609 B2
(45) Date of Patent: Jun. 23, 2020

(54) IMPEDANCE SPECTROMETER WITH PROGRAMMABLE ELEMENTS

(71) Applicant: William N Carr, Cary, NC (US)

(72) Inventor: William N Carr, Cary, NC (US)

( * ) Notice: Subject to any disclaimer, the term of this patent is extended or adjusted under 35 U.S.C. 154(b) by 0 days.

(21) Appl. No.: 16/693,375

(22) Filed: Nov. 25, 2019

(65) Prior Publication Data

US 2020/0124553 A1 Apr. 23, 2020

Related U.S. Application Data

(63) Continuation of application No. 16/059,237, filed on Aug. 9, 2018, now Pat. No. 10,551,334.

(51) Int. Cl.
*G01N 27/02* (2006.01)

(52) U.S. Cl.
CPC .................. *G01N 27/026* (2013.01)

(58) Field of Classification Search
CPC .... G01N 22/00; G01N 22/04; G01R 29/0814; G01R 29/0878; G01R 31/002
USPC ......................................................... 324/632
See application file for complete search history.

(56) References Cited

U.S. PATENT DOCUMENTS

| | | | | |
|---|---|---|---|---|
| 3,694,737 A * | 9/1972 | Busker | ................... | G01N 22/04 324/640 |
| 3,715,667 A * | 2/1973 | Nicolson | ................ | G01N 22/02 324/637 |
| 5,187,443 A * | 2/1993 | Bereskin | .............. | G01R 1/0408 324/632 |
| 5,500,599 A * | 3/1996 | Stange | ................... | G01N 22/00 324/632 |
| 5,909,159 A * | 6/1999 | Remillard | ............... | H01P 1/208 333/202 |
| 6,839,035 B1* | 1/2005 | Addonisio | ......... | G06K 7/10178 340/572.1 |
| 7,315,173 B2* | 1/2008 | Funato | ............... | G01R 29/0814 324/452 |
| 7,336,230 B2* | 2/2008 | Lee | .................... | G01R 29/0828 324/627 |
| 8,542,122 B2* | 9/2013 | Goodnow | .......... | A61B 5/14532 340/572.1 |
| 9,460,320 B2* | 10/2016 | Ieki | ...................... | G06K 7/0008 |
| 2005/0073321 A1* | 4/2005 | Kohler | ................... | G01N 22/04 324/640 |
| 2007/0146138 A1* | 6/2007 | Phipps | ............... | G06K 7/10178 340/572.7 |

(Continued)

*Primary Examiner* — Christopher P McAndrew

(57) ABSTRACT

A system and method for sensing wave impedance of a material using an RF power source with a sensor structure comprised of a resonant electromagnetic radiative filter (MEF). The wave impedance is determined by processing a differential RF signal level within an interrogator comprising an impedance calculator. A differential RF signal between a source signal level and a response signal level affected by field coupling of the REF with a material of interest. In embodiments based on frequency scanning transmissometry (FST), the impedance spectrometer determines both the real and imaginary part of the wave impedance of the material. In embodiments the impedance spectrometer comprises an RFID transponder. In embodiments, the interrogator is disposed as payload on a UAV drone. In embodiments, the impedance spectrometer is a node within a communications network.

20 Claims, 12 Drawing Sheets

(56) References Cited

U.S. PATENT DOCUMENTS

| | | | | |
|---|---|---|---|---|
| 2007/0262869 | A1* | 11/2007 | Young | G06K 7/10336 340/572.7 |
| 2008/0303717 | A1* | 12/2008 | Durban | G01S 1/44 342/371 |
| 2010/0066386 | A1* | 3/2010 | Dos Santos | G01N 22/04 324/640 |
| 2010/0161004 | A1* | 6/2010 | Najafi | A61N 1/3787 607/60 |
| 2010/0231407 | A1* | 9/2010 | Carr | G06K 19/0723 340/691.1 |
| 2010/0271188 | A1* | 10/2010 | Nysen | G01S 13/755 340/10.41 |
| 2012/0001730 | A1* | 1/2012 | Potyrailo | G06K 19/0717 340/10.1 |
| 2012/0004851 | A1* | 1/2012 | Potyrailo | G01N 33/0073 702/19 |
| 2012/0190310 | A1* | 7/2012 | Ieki | G06K 7/0008 455/73 |
| 2012/0256733 | A1* | 10/2012 | Carr | G06K 19/0723 340/10.51 |
| 2012/0286935 | A1* | 11/2012 | Huang | G01D 21/00 340/10.1 |
| 2013/0109305 | A1* | 5/2013 | Savoj | G06K 7/0008 455/41.1 |
| 2014/0182363 | A1* | 7/2014 | Potyrailo | G01N 27/026 73/64.53 |
| 2014/0224989 | A1* | 8/2014 | Long | G02F 1/0126 250/338.4 |
| 2018/0202961 | A1* | 7/2018 | Sussner | G01N 29/036 |

* cited by examiner

IMPEDANCE SPECTROMETER WITH PROGRAMMABLE ELEMENTS

CROSS REFERENCE TO RELATED APPLICATIONS

This application is a continuation of U.S. patent application Ser. No. 16/059,237 filed Aug. 9, 2018. U.S. patent application Ser. No. 16/059,237 is a continuation-in-part of U.S. patent application Ser. No. 15/507,215 with PCT WO2016/033561 filed Aug. 28, 2015 and issued as U.S. Pat. No. 10,101,288 on Oct. 16, 2018.

The underlying concepts, but not necessarily the language, of the following cases are incorporated by reference:

U.S. Provisional Application 62/043,376 filed Aug. 28, 2014

U.S. Provisional Application 62/106,805 filed Jan. 23, 2015

U.S. Provisional Application 62/210,888 filed Aug. 28, 2015

If there are any contradictions or inconsistencies in language between this application and one or more of the cases that have been incorporated by reference that might affect the interpretation of the claims in this case, the claims in the case should be interpreted to be consistent with the language in this case.

This case claims benefit of the following provisional applications:

U.S. Provisional Application 62/043,376
U.S. Provisional Application 62/106,805
U.S. Provisional Application 62/210,888

FIELD OF THE INVENTION

The present invention relates to wireless sensors in general, and, more particularly, to wireless sensors based on resonant filter structures.

BACKGROUND OF THE INVENTION

A material's properties can be summarized by a material parameter known as the "wave impedance" (or simply "impedance") of the material, which is a complex number. A good discussion of the relationship between wave impedance and permittivity, permeability, and conductivity is available, at the time of writing this disclosure, in the Wikipedia entry for wave impedance: http//en.wikipedia.org/wiki/wave impedance.

Many materials of interest are nonconductive and non-magnetic. For such materials, permeability does not play a role, and there is a simple, one-to-one relationship between the impedance of the material and the material's permittivity, such that measuring the permittivity and measuring the impedance of the material are equivalent. Impedance spectroscopy is also often referred to as dielectric spectroscopy and vice versa.

Instruments for determining the wave impedance of a material have been developed using many different sensing technologies that comprise separate components operating with different electromagnetic modalities. These instruments include capacitive sensors wherein the resonant tank circuit of a Colpitts, Clapp, or Hartley LC oscillator is affected by exposure to a material of interest. The wave impedance of the material affects the oscillation frequency the LC oscillator. An example of such a sensor is disclosed by in U.S. Pat. No. 5,418,466 wherein a tuned circuit oscillates at a frequency representative of the complex dielectric constant of the medium.

In applications wherein the objective is to sense both the real and imaginary parts of a wave impedance, multiple measurements are required. It is fundamentally impossible to derive the values of two independent unknown quantities from a single measurement. In general, sensors such as a capacitance sensor wherein a material of complex permittivity affects the oscillation frequency of an LC resonant circuit, accuracy for measurement of complex impedance is limited due to nonlinear cross modulation effects relating to the real and imaginary parts of material permittivity.

Another class of instruments for sensing wave impedance of a material is based on time delay reflectometry (TDR) and time delay transmissometry (TDT) wherein the propagation speed of a wave along a transmission line is measured. When the transmission line is exposed to a material, the propagation speed of signal through the transmission line is affected. TDR and TDT sensors generally require delay measurements in the picosecond range for useful accuracy. limitations for TDR and TDT sensing include requirement for a length of transmission line adequate to obtain sufficient propagation delay and economic considerations involved with maintaining stability within a picosecond delay timer.

An application wherein wave impedance affects a communication link is disclosed in U.S. Pat. No. 6,593,886. The apparatus disclosed here is a planar loop antenna with a balun.

A prior art example of a sensor antenna coupled into an adjacent medium is disclosed in U.S. Pat. No. 9,916,528. The signal strength of RF energy emitted by an RFID tag is affected by the frozen or thawed state of a material disposed proximally with the tag.

An RFID sensor arrangement for determining a degradation condition within a material is disclosed in U.S. Patent Application 2010/0090802 A1. Reference to a material wave impedance is not detailed.

An early paper disclosing a split ring resonator with negative permittivity is D. R. Smith et al, "Determination of negative permittivity and permeability of metamaterials from reflection and transmission coefficients", Physical Review B, November, 2001; doi: 10.1103/PhysRevB.65.195104.

There is a need for improved impedance spectrometry for determining permittivity of a material with improved accuracy and lower cost for sensing the real and imaginary parts of the wave impedance of a material. Instruments are needed to provide increased accuracy, reduced cost, portability, imbedded sensing and operation within networks including a mesh drone network and a WLAN cellular network.

SUMMARY OF THE INVENTION

The present invention provides an impedance spectrometer comprising a resonant electromagnetic filter (REF) which couples an electromagnetic field into a material of interest for the purpose of determining the real part and/or imaginary part of the wave impedance of a material of interest. An innovative feature of the impedance spectrometer is that complex wave impedance of a material is determined in some embodiments using scanning frequency transmissometry (SFT) wherein the real and imaginary part of material wave impedance are determined by sensing at a plurality of frequencies.

In embodiments, the impedance spectrometer comprises an interrogator controlling a sensor structure through operative couplings with a transmitter T and one or more receivers R. In some embodiments, the transmitter T and the receiver R functions are provided by a transceiver TR. The response signal at receiver R is affected by RF material field-coupling through a resonant electromagnetic filter (REF), wherein the REF is field-coupled with the transmitter T and receiver R. Field-coupling with the material is affected by the real and imaginary components of the permittivity of a material of interest. The interrogator comprises an impedance calculator for calculating the wave impedance of a material based on processing of signal levels affected by the material field-coupling. The interrogator also comprises a control/communications link. In embodiments, the communications link comprises one or more of an interface with an RF mesh network, a local area network (LAN) and/or a cellular WLAN network. In embodiments, the sensing structure is disposed at least in part within the same enclosure as the integrator, and the sensing structure is operatively coupled with the integrator by wired and/or wireless means. In embodiments the communications link includes a mesh network node either disposed in a fixed position or carried as payload on a UAV drone.

The impedance calculator determines the real part and/or imaginary part of the wave impedance of the material based on one or more sensing operations, wherein each sensing operation measures a difference-signal level $\Delta V_s$ between the RF source signal and the RF response signal at a controlled frequency.

FIG. 1A depicts a first embodiment of the impedance spectrometer 100A comprised of a sensing structure 109 and an interrogator 101. In this embodiment the sensor structure 109 is disposed within a material of interest 109, The impedance spectrometer determines the wave impedance of material 109 in this invention. In embodiments, the receiver (R1) and transmitter (T1) communicate with the interrogator which may be at least partially disposed in a stationary location, carried as a handheld unit, or as payload on a UAV drone. In some embodiments, the interrogator may be disposed on one end of a wand stick and the sensing structure are disposed on the other end of the wand stick. The wand stick is useful for probing various materials including soils, grains, liquids, peanuts, and a variety of agricultural products.

In FIG. 1A the RF source signal from transmitter T1 103 material field-couples 131 with material of interest 108 through resonant electromagnetic filter REF 106. Material field coupling 131 affects the response signal received into receiver R1 102. Transmitter T1 103, receiver R1 102 and resonant electromagnetic filter REF 106 comprise a sensing structure 109

In the depiction of FIG. 1A, an impedance calculator within interrogator 101 processes the source signal level and the response signal level to determine the wave impedance of the material 108. In embodiments, the impedance spectrometer the sensor structure is adapted to comprise one or more transceivers programmed for operation as either the transmitter or the receiver FIG. 1B depicts a second embodiment of the impedance spectrometer 100B wherein the interrogator 101 and transmitter T1 103 are disposed together. This configuration is generally configured to operate as a passive RFID system wherein the receiver 102 is disposed near the surface of material 108 with field coupling into the resonant electromagnetic filter (REF) 106. The operative coupling 130 from the transmitter (T1) 103 couples into both the material (108) and the receiver (R1) 102. Operative coupling from the receiver (R1) provides a difference signal to the interrogator.

The operative coupling 130 between the transmitter 103 and the receiver 102 is also field-coupled 131 with the material 108 through a resonant electromagnetic filter REF 106. Applications for the embodiment of FIG. 1B include the use of an interrogator and transmitter (T1) 103 as payload on a UAV drone. The system is calibrated based on the signal path that includes couplings 104, 130 selected as wireless. In other embodiments, couplings 104,130 may be configured as a wired bus connection to a handheld or stationary interrogator. I FIG. 1C depicts a third embodiment 100C of the impedance spectrometer wherein the interrogator 101 and transmitter T1 103 are disposed together. The operative coupling between the interrogator 101 and the transmitter (T1) 103 is a digital bus link. The resonant electromagnetic filter (REF) is disposed within the material of interest 108. Operative coupling 130 between the transmitter 103 and receiver (R1) 102 comprises antenna 1, wireless link 130, antenna 113, and RF range extender 115. An RF signal originating from the transmitter (T1) is coupled with receiver (R1) 102 and material 105 through a resonant electromagnetic filter (REF) 106. This embodiment generally is configured as a passive or semi-passive RFID system wherein communication from the receiver (T1) 102 return to the interrogator is through the same coupling as the transmitter to receiver. In the RFID system embodiment, the return signal from the receiver is obtained by modulating the reflected transmitter signal as an RF data link. The embodiment depicted in FIG. 1C is generally configured with receivers 102, 116 as very low cost RFID passive transponders. In this embodiment, the RF transmitter source signal level is defined as the signal level at transmitter (T1) 103 and the response signal level is defined as the signal level sensed at the interrogator as received from receiver (R1) 102

The spectrometer depicted in FIG. 1C also includes a reference receiver 116 generally disposed very near the surface or external to the material 108. The operative link 132 with the interrogator is an RF data link, wherein the data link from receiver to interrogator includes antenna3 and wireless operative coupling 132. Antenna3 does not field-couple with material 108 and provides a reference sensor signal that is used by a receiver co-disposed with the interrogator 101 and transmitter 103. In this embodiment, the reference receiver 116 provides a reference return signal level to the interrogator and is used to calibrate the system for RF signal attenuation over the air path between interrogator and the material of interest. 109. In this embodiment, the RF response signal is defined as the RF signal received at the interrogator through the operative coupling 132.

FIGS. 2A and 2B are diagrams of the RF response of a single-pole resonant filter or RF antenna field-coupled with a material. In this invention, the resonant filter is designated as a resonant electromagnetic filter (REF). Response is expressed as decibels (dB) of return loss $S_{11}$. This way of representing response of a filter response is well known in the art.

FIG. 2A is a simulation depicting response of a resonant filter affected by values of the real part of wave impedance of a surrounding material. In this disclosure we disclose an impedance spectrometer for sensing a non-magnetic material. In this disclosure the terms wave impedance and permittivity are used interchangeably. This diagram shows six curves corresponding to six possible values of the real part of the permittivity. It is customary, in the art, to express permittivity as $\varepsilon=\varepsilon'-j\varepsilon''$ wherein $\varepsilon'$ and $\varepsilon''$ are the real and imaginary parts of the permittivity vector, respectively. The symbol $\varepsilon'$ is also known as the dielectric constant. The six parametric curves of FIG. 2A show clearly that the filter response is substantially affected by changes in $\varepsilon'$. Each of the six curves shows antenna return loss as a function of frequency for the indicated value of $\varepsilon'$. In particular, the curves were generated for a resonant filter interrogated at frequency $f_o=1$ GHz assuming the value $\varepsilon'=1$ for the real part of the permittivity. Accordingly, curve 201 shows that minimum return loss occurs at the resonant frequency of $f_o=1$ GHz when $\varepsilon'=1$ corresponding to free space. When the value of $\varepsilon'$ is greater than 1, minimum return loss occurs at a frequency different from the nominal resonant frequency, and the minimum is not as low. We expressly note that in this example, a measurement of the response level at a frequency $f_o$ higher than the resonant frequency of the resonant filter is uniquely related to the real part $\varepsilon'$ of the material permittivity. Measurements based on this uniqueness are used in this invention to determine the real part of a material permittivity. For example, a useful frequency for coupling through the filter of FIG. 2A is 1.05 GHz.

FIG. 2B is a simulation depicting response of a resonant single-pole filter affected by values of the imaginary part $\varepsilon''$ of the wave impedance of surrounding material. In this diagram the response of a resonant circuit is plotted for a specific material as a function of frequency with loss tangent $\delta$ as a parameter. Loss tangent $\delta$ is defined as the ratio of real to imaginary parts of permittivity wherein loss tangent $\delta=\varepsilon'/\varepsilon''$. In FIG. 2B four loss tangent $\delta$ values are shown as parameter. We expressly note here that at the filter response measured at the filter resonant frequency 0.815 GHz uniquely defines the loss tangent $\delta$ as is clearly shown in FIG. 2B. Measurements based on this uniqueness are used in this invention to determine the imaginary part of the wave impedance $\varepsilon'$. More specifically, a first measurement of response at a frequency higher than the resonant frequency of the filter uniquely determines the value of $\varepsilon'$ for a material of interest.

From the example FIG. 2A it is noted that the resonant frequency of the filter field-coupled with the material is also uniquely indicated by sensing at the example frequency 1.05 GHz. The response of the resonant filter shown in FIG. 2B at its resonant frequency 0.815 GHz is used to uniquely determine the imaginary part of the material permittivity based on calibration of the impedance spectrometer based on materials of known response at a controlled frequency, such as the two frequencies 1.05 and 0.815 GHz in this example. The value for loss tangent is uniquely defined for any specific material that has been calibrated to obtain the reference curves as illustrated in FIG. 2B. The imaginary part of the wave impedance of the material can be obtained wherein the real part $\varepsilon'$ of the wave impedance is determined with a first measurement of filter response at a frequency higher than the filter resonant frequency, followed by a second measurement of the filter response at its resonant frequency. First a value for $\varepsilon'$ is determined with the first measurement obtained at a higher frequency, and followed by a second measurement at the lower resonant frequency to determine the loss tangent $\delta$.

$\varepsilon''=\varepsilon'/\text{loss tangent } \delta$

In embodiments where increased accuracy for the imaginary part of wave impedance is desired, the resonant frequency of the filter coupled with the material may be obtained by scanning the signal frequency over a range that includes the resonant frequency. A method schedule for determining the wave impedance using the impedance spectrometer of this invention involves use of an algorithm or look-up table and RF response signal measurements obtained with a known material calibrated using an accurate sensor of maximum accuracy such as a TDR, TDT or material doped with accurately weighed components.

A method for determining a real and/or imaginary component of a wave impedance of a material comprising a plurality of sensing operations based on calculations implemented in an impedance calculator implementing an algorithm or lookup table is presented as follows. A sensing operation comprises:

transmitting an RF source signal at a controlled frequency from an RF transmitter (T1), wherein the RF source signal is field-coupled through a resonant electromagnetic filter (REF) into a material receiving the RF response signal from the RF transmitter (T1) into an RF receiver (R1).

measuring a difference-signal level $\Delta V_s$ between the RF source signal and the RF response signal, wherein the difference-signal level $\lambda V_s$ is affected by the wave impedance of the material;

creating a plurality of difference signal databases comprising one or more difference signal levels $\Delta V_s$ wherein the first difference signal database is created using a material of known wave impedance and the second difference signal database is created using a material of unknown wave impedance.

A first calculation is performed in the impedance calculator using the first and second difference signal databases, wherein the controlled frequency is higher than the resonant frequency of the resonant electromagnetic filter (REF), and further wherein said first and second difference signal databases are processed with an algorithmic- or lookup-table formula to determine a real component of the wave impedance of the material; a second calculation is performed in the impedance calculator using the first and second difference signal databases, wherein the controlled frequency is the same as the resonant frequency of the resonant electromagnetic filter (REF), and further wherein said first and second difference signal databases are processed with an algorithmic- or lookup-table formula together with the real component of the wave impedance of the material to determine both the loss tangent $\delta$ and the imaginary component of the wave impedance of the material.

The resonant electromagnetic filter (REF) used in embodiments is typically a two-terminal, single pole, structure. This structure can be an LC tank circuit, a resonant antenna, or a metamaterial. FIG. 3 depicts plan views of resonant filters comprising exemplary metamaterial resonant electromagnetic filter (MREF) structures comprising one or more of a split ring resonator (SRR) in inserts 301, 303, 304, 305, and 307. Insert 302 depicts a complementary split ring resonator CSRR filter. Other types of MREF structures include insert 306, coupled spiral resonators and fractile metamaterial resonators. In addition, MREF structures may comprise variations and combinations of the exemplary MREF structures of FIG. 3.

In embodiments, the signal-coupling between the transmitter and the receiver is obtained through a strip waveguide, and the strip waveguide is material field-coupled with the REF. In some embodiments, the strip waveguide comprises an RF communications antenna, and further wherein the operative-couplings with the interrogator comprise wireless links, the wireless links comprising communication/control links between the sensing structure and the interrogator.

In embodiments, the operative-coupling with the interrogator comprises a wireless communications/control links operated at a frequency the same or different from the RF source signal.

In embodiments, the resonant electromagnetic filter REF is disposed immediately proximal to or embedded within the material of interest.

In embodiments, the transmitter and the receiver are disposed within the same enclosure or on the same printed circuit board.

In embodiments, the impedance spectrometer is adapted with a digital clock, the digital clock enabling operation of the impedance spectrometer at specific, programmed time intervals.

In embodiments the transmitter and the receiver are operatively-coupled with a mobile phone through a wired databus or a wireless link, the mobile phone comprising at least a portion of the interrogator.

In embodiments, at least a portion of the impedance spectrometer is partially-powered by an energy harvester, the energy harvester receiving energy from one or more of RF, solar, thermoelectric or piezoelectric energy harvesting sources.

In embodiments, the interrogator is at least partially disposed as payload on an unmanned aerial vehicle (drone) and the sensor structure is disposed in close proximity or within the material.

In applications, the material of interest comprises an agricultural product, in raw or processed form, selected from a group comprised of maize, cocoa, coffee, wheat, barley, ta, nuts, peanuts, tree oils, timber, bales of hay, silage and selected plant leaf.

In applications, the material of interest comprises one or more of beer, wine, rum and industrial chemicals, the material further comprised of at least two components, the components having a different real part of wave impedance, In applications, the material of interest comprises setting cement, wherein the wave impedance of the setting cement changes with time as the cement cures.

DETAIL DESCRIPTION

Definitions

The following terms are defined for use in this disclosure and the appended claims:

"interrogator" means the device comprising the control/communications circuits and an impedance calculator. The interrogator controls the sensing structure and may be disposed within a single enclosure or distributed as component parts.

"transmitter" means the device providing the RF source within the sensing structure with field-coupling into a material of interest.

"receiver" means the device within the sensing structure receiving the RF response signal coupled from the transmitter as affected by field-coupling with a material of interest.

"operative coupling" means a wired and/or wireless means of coupling between an interrogator and a sensor structure. The coupling may comprise a digital data link and/or analog RF link. The coupling may comprise a databus digital link and/or a wired databus link.

"resonant electromagnetic filter" or "REF" means a resonant filter comprising LC resonant elements field-coupling with a material of interest, the field-coupling affecting an RF response signal from the receiver (R1).

"metamaterial resonant electromagnetic filter" or "MREF" means a type of resonant electromagnetic filter (REF) wherein the field-coupling comprises at least one of an electric, electromagnetic or magnetic field, and the MREF is operational with at least one of negative permittivity or negative permeability.

"passive RFID system" means a system comprising an interrogator, wherein a transmitter within the interrogator supplies operational power and control signals to a receiver integral to a remotely-disposed RFID tag through a wireless operative coupling link. The RFID tag communicates to the interrogator by modulating a reflected RF signal originating from the transmitter.

Figure 4:
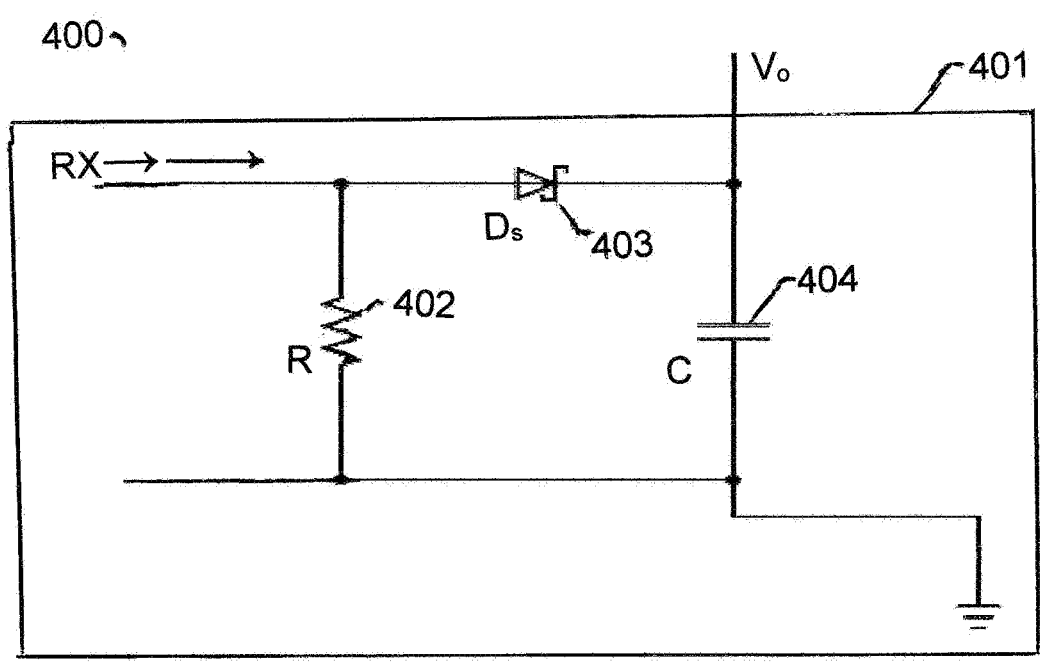
FIG. 4 is a circuit diagram depicting an RF detector for use in conjunction with embodiments of the invention.

FIG. 4 is a circuit diagram depicting an RF receiver (R1) 401 receiving a response signal RX from the transmitter T1. The circuit comprises a load resistor 402, a Schottky diode 403, and smoothing capacitor 404 with dc output voltage $V_o$. This circuit is a passive device generally bus-connected with a local microcontroller.

Figure 5:
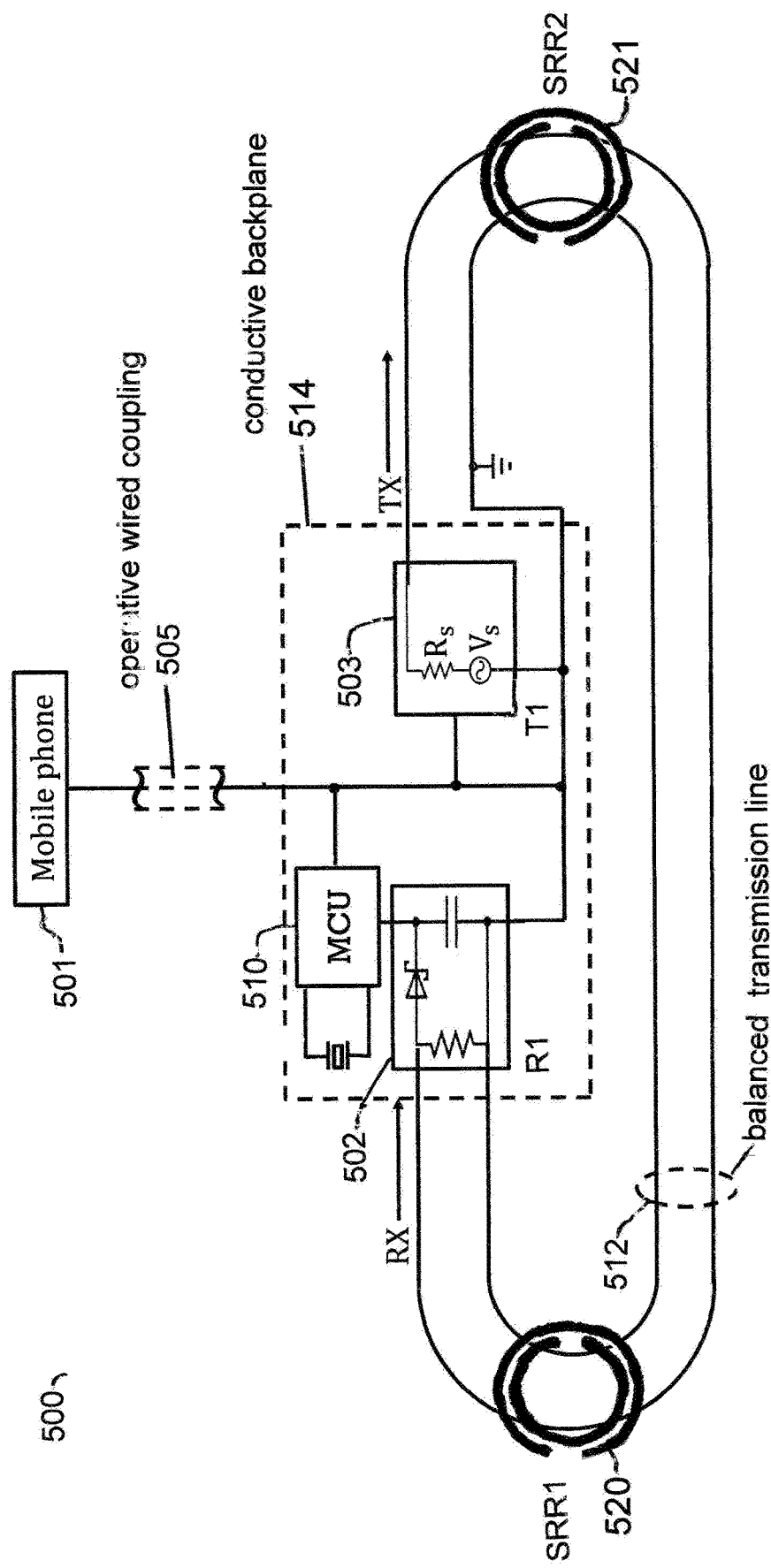
FIG. 5 depicts an embodiment comprising the RF detector of FIG. 4 and dual SRR MREF filters with field-coupling to a material in accordance with the present teachings.

FIG. 5 depicts an embodiment comprising the RF detector 502 from FIG. 4 and dual split ring resonator SRR MREF filters 520, 521. The MREFs are material field-coupled with a material of interest. The sensing structure depicted here comprises a transmitter sending an RF signal TX into a balanced transmission line 512 that field-coupled with the MREF filters 520, 521. Local control for the sensing structure is performed by the microcontroller unit MCU 510. The integrator in this embodiment is a mobile phone 501 connected with the MCU, T1 and R1 elements through a databus operative coupling 505. The MCU, T1 and R1 elements are disposed on a printed circuit board having conductive backplane 514. The balanced transmission line 512 comprises a metal trace disposed on the printed circuit board surface opposite to the traces comprising the MREF structures.

Figure 6:
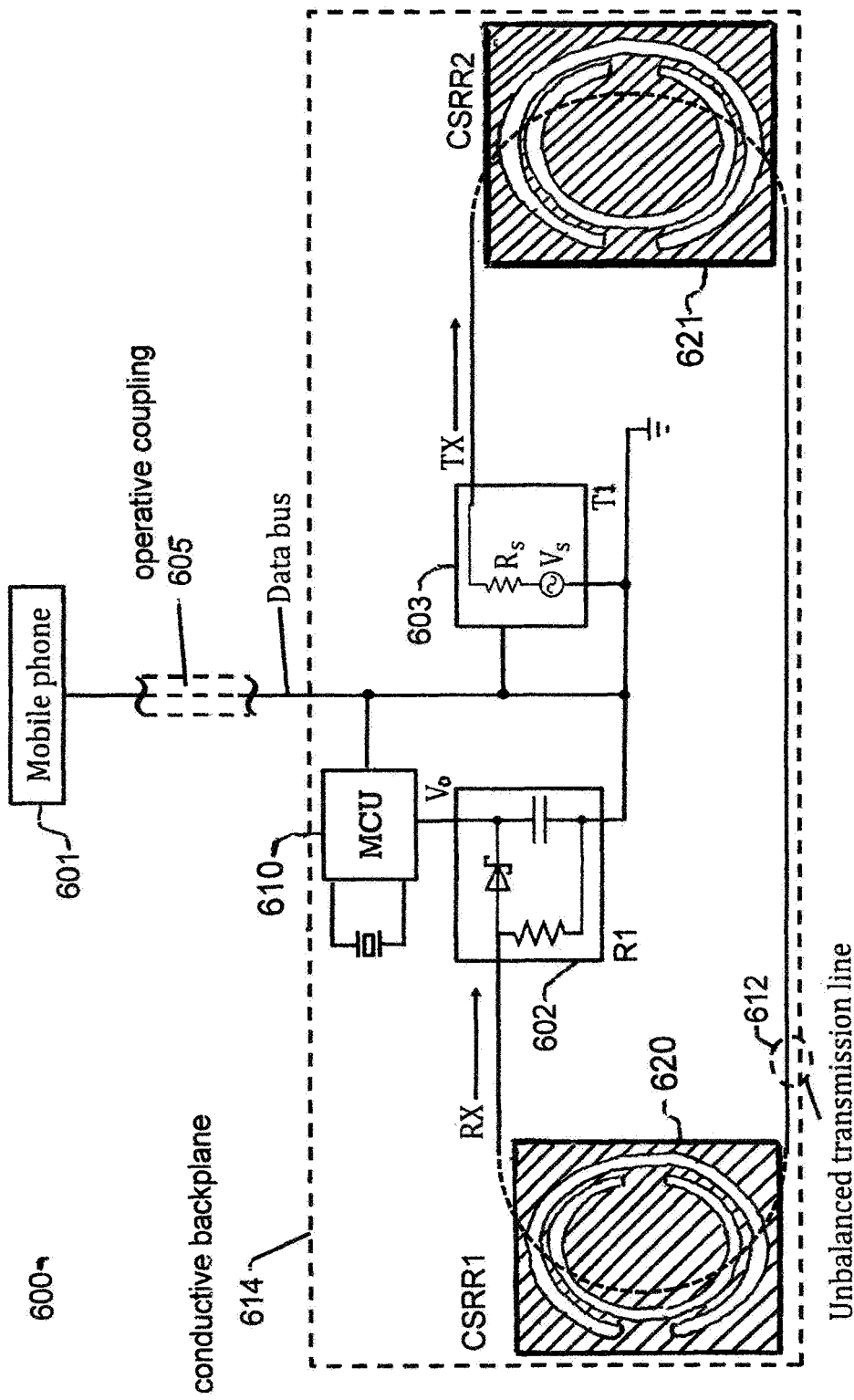
FIG. 6 depicts an embodiment the RF detector R1 of FIG. 4 and a transmitter T1 with dual CSRR MREF filters providing increased sensitivity in accordance with the present teachings.

FIG. 6 depicts an embodiment wherein the MREF comprises two complementary split ring resonators CSRR 620, 621. The MREFs are material field-coupled with a material of interest. The sensing structure depicted here comprises a transmitter sending an RF signal TX into an unbalanced transmission line 612 that field-coupled with the MREF filters 620, 621. Local control for the sensing structure is performed by the microcontroller unit MCU 510. The integrator in this embodiment is a mobile phone 601 connected with the MCU, T1 and R1 elements through databus operative coupling 605. The entire sensing structure is disposed on a printed circuit board having conductive backplane 614. The balanced transmission line 612 comprises a metal trace disposed on the printed circuit board surface opposite to the MREF filters. The two MREF traces a defined by the absence of circuit board metallization.

Figure 7:
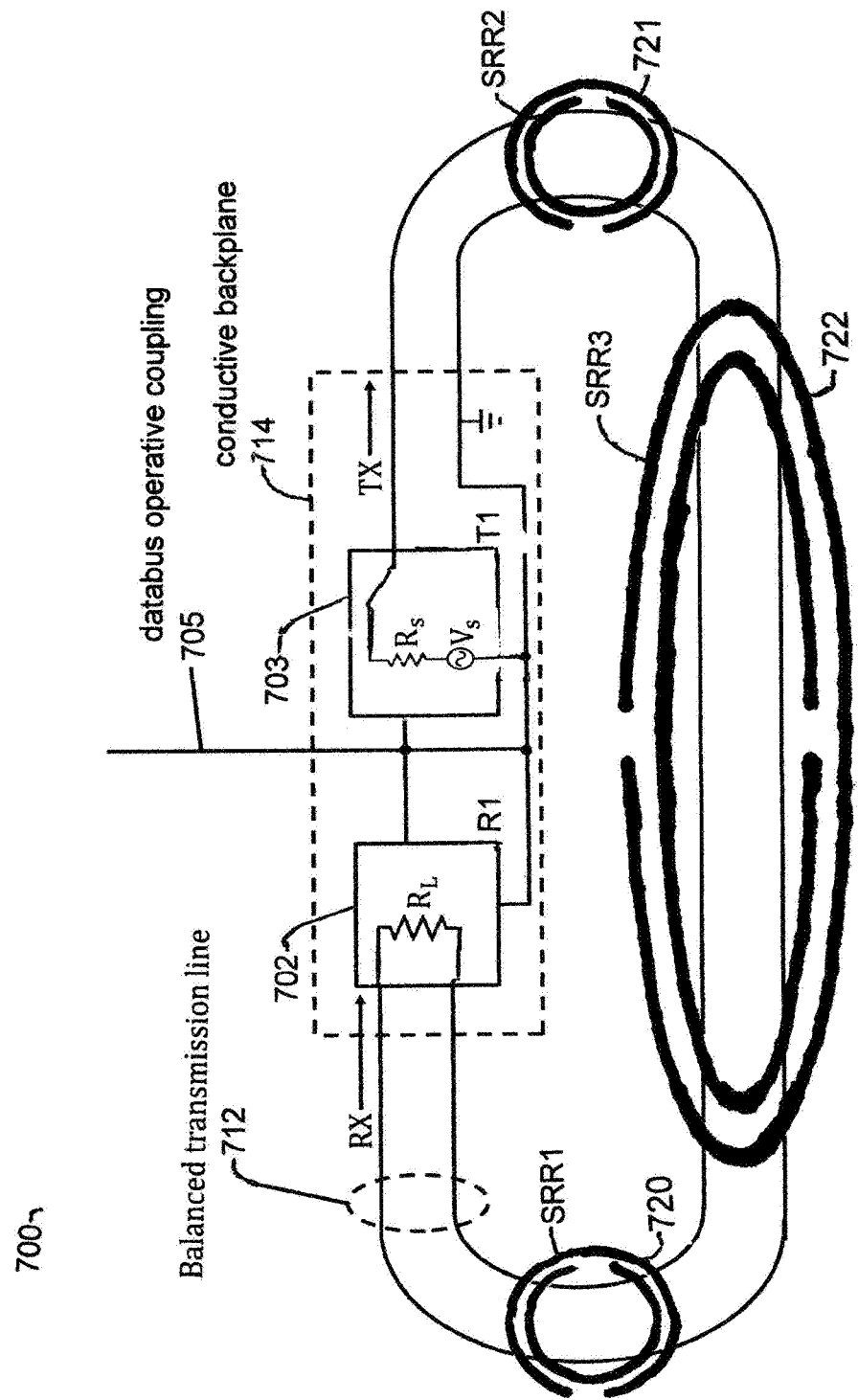
FIG. 7 depicts an embodiment having a databus operative coupling and field-coupled SRR MREF filters tuned for a plurality of frequencies in accordance with the present teachings.

FIG. 7 depicts an embodiment having a databus operative coupling and field-coupled SRR MREF filters tuned for a plurality of frequencies. FIG. 7 depicts an embodiment wherein the MREF comprises two complementary split ring resonators 720, 721. The MREFs are material field-coupled with a material of interest. The sensing structure depicted here comprises transmitter T1 sending an RF signal TX into balanced transmission line 722. The transmission line field-couples into MREF filters 720, 721. In this embodiment, control for the sensing structure is obtained with the interrogator and the microcontroller MCU connected to an extended portion of databus 705. In embodiments, the interrogator and microcontroller MCU are provided by a mobile phone The entire transmitter T1 and receiver R1 are disposed on a printed circuit board having conductive backplane 714. Traces to define the MREF structures 720, 721 are patterned on the printed circuit board surface opposite to the balanced transmission line 722.

Figure 8:
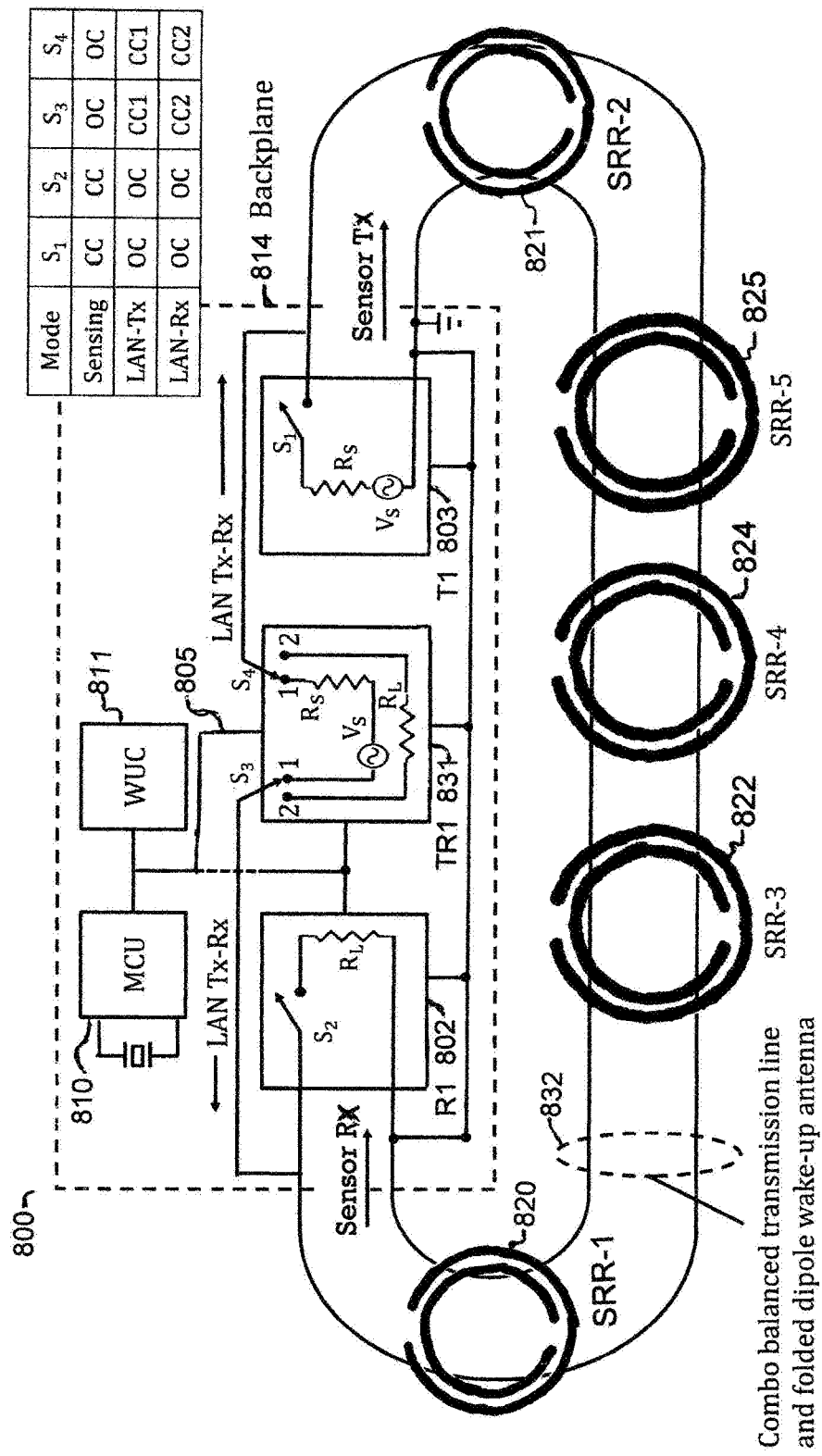
FIG. 8 depicts an embodiment comprising a transmitter, a receiver and a transponder with a plurality of SRR MREF filters tuned to a plurality of frequencies, wherein the transmission line comprises an antenna for operation within a LAN in accordance with the present teachings.

FIG. 8 depicts an embodiment wherein the sensing structure operates autonomously as a node within a LAN network. The sensing structure is powered locally, typically by a battery and comprises MCU 810, wake-up clock 811, transmitter T1 803, receiver R1 802 and a communications transceiver TR1 831. Elements of the sensing structure are connected via databus 811. Local control is provided by the MCU 810. In some embodiments, the wake-up clock WUC is programmed to initiate autonomous sensing operations. The sensing structure comprises five MREF filters 820, 821, 822, 824, 825 tuned to a plurality of frequencies. Multiple MREF filters are field-coupled with the balanced transmission line 832 between the transmitter (T1) signal source SensorTx and the receiver (R1) for the response signal SensorRx. Multiple MREF filters tuned to the same frequency increase sensitivity for wave impedance determinations. In some embodiments, some MREFs are tuned to a higher frequency providing increased sensitivity to measurement of the real part of permittivity and some MREFs are tuned to a lower frequency wherein providing increased sensitivity to measurement of the imaginary part of permittivity. A sensing operation is enabled by the MCU 810 wherein switch $S_2$ of receiver R1 802 is in closed circuit (cc) position, and switch $S_1$ of transmitter T1 803 is in closed circuit (cc) position. Transceiver TR1 831 is disabled for sensing operations.

For operation as a node within a local area network LAN, transceiver TR1 is enabled as a transmitter with switch $S_3$ in the closed circuit position 1 (CC1) and switch $S_4$ in the closed circuit position 1 (CC1). The circuit is enabled as a receiver within a local area network LAN with switch $S_3$ in circuit position CC2 and switch $S_4$ in circuit position CC2.

In embodiments, the sensing structure of FIG. 8 may communicate with an interrogator disposed as payload on a UAV drone. The interrogator may be disposed at a distance from the sensing circuit. In embodiments, the sensing circuit of FIG. 8 may be disposed proximal to or buried within the material of interest.

In some embodiments based on the sensing structure of FIG. 8, the wake-up clock is provided to enable receiver and/or transmitter operation at predetermined times of day. In some applications, the sensing structure operates in a transmit-only communications mode in order to conserve battery power.

Figure 9:
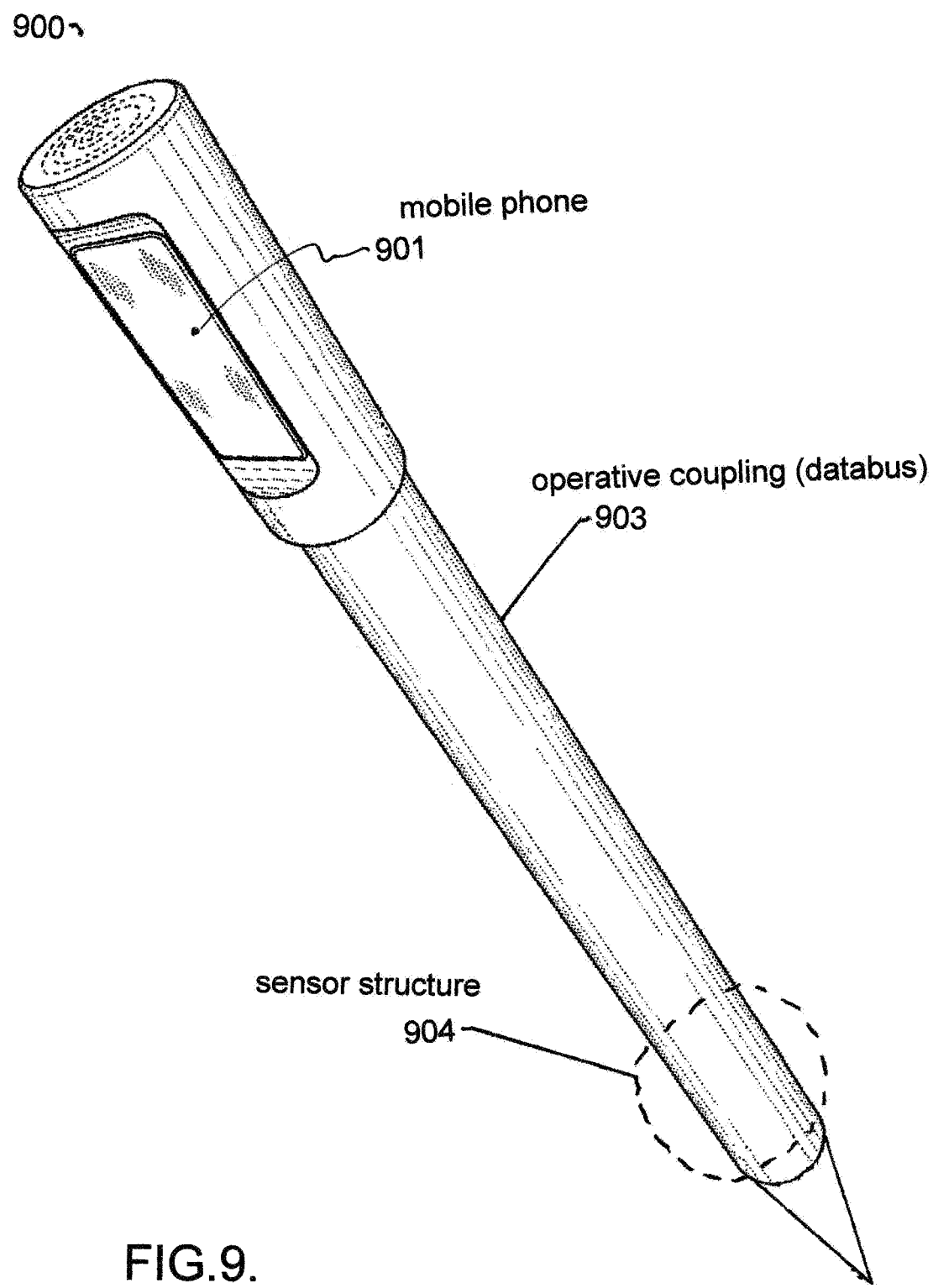
FIG. 9 depicts the spectrometer in the form of a stick wand with a mobile phone in accordance with the present teachings.

FIG. 9 depicts the spectrometer in the form of a stick wand with a mobile phone. The mobile phone 901 comprises the interrogator, the interrogator connected with sensor structure 904 through operative coupling 903.

Figure 1A:
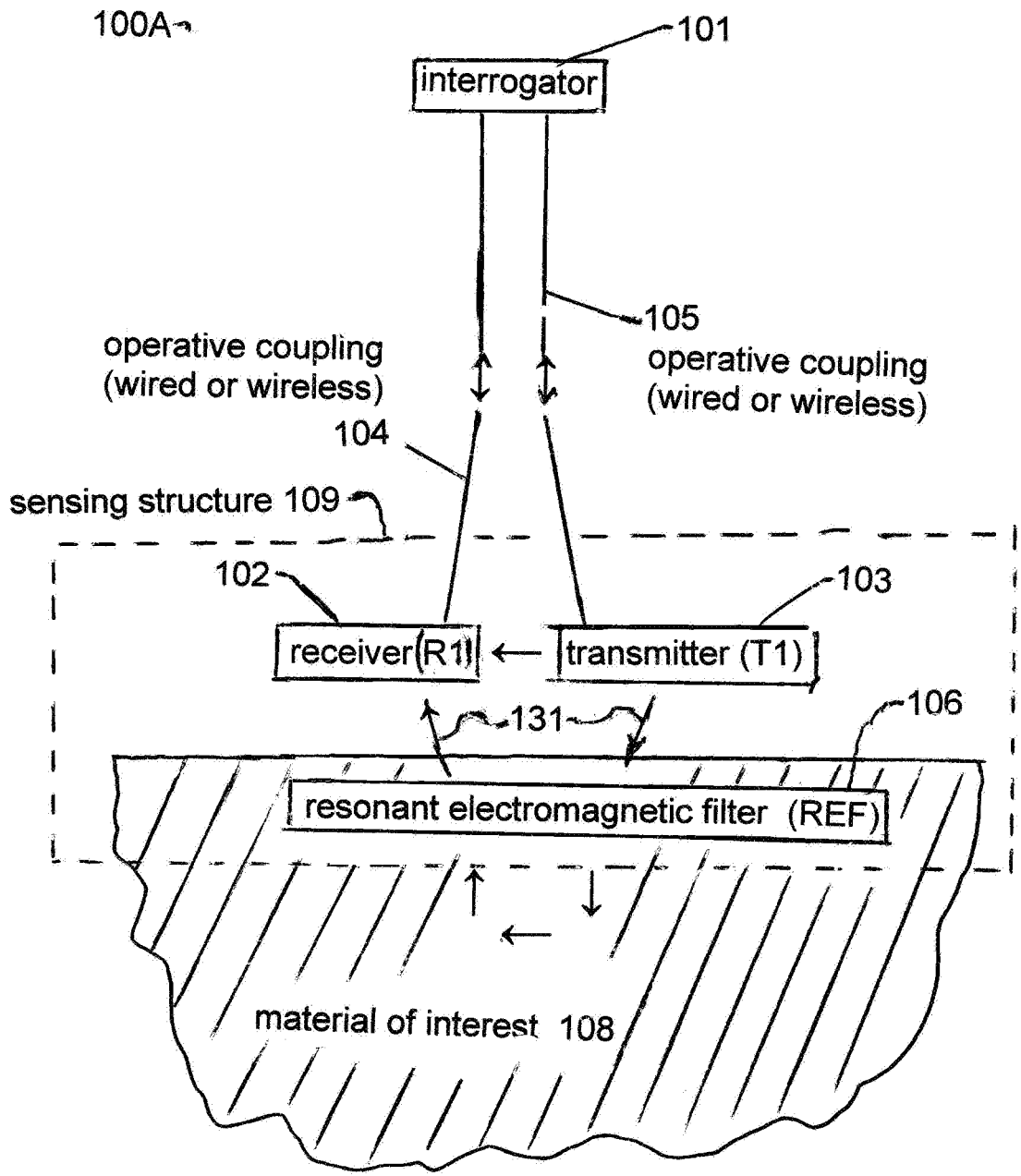
FIG. 1A depicts a first configuration in accordance with an embodiment of the invention.
Figure 1B:
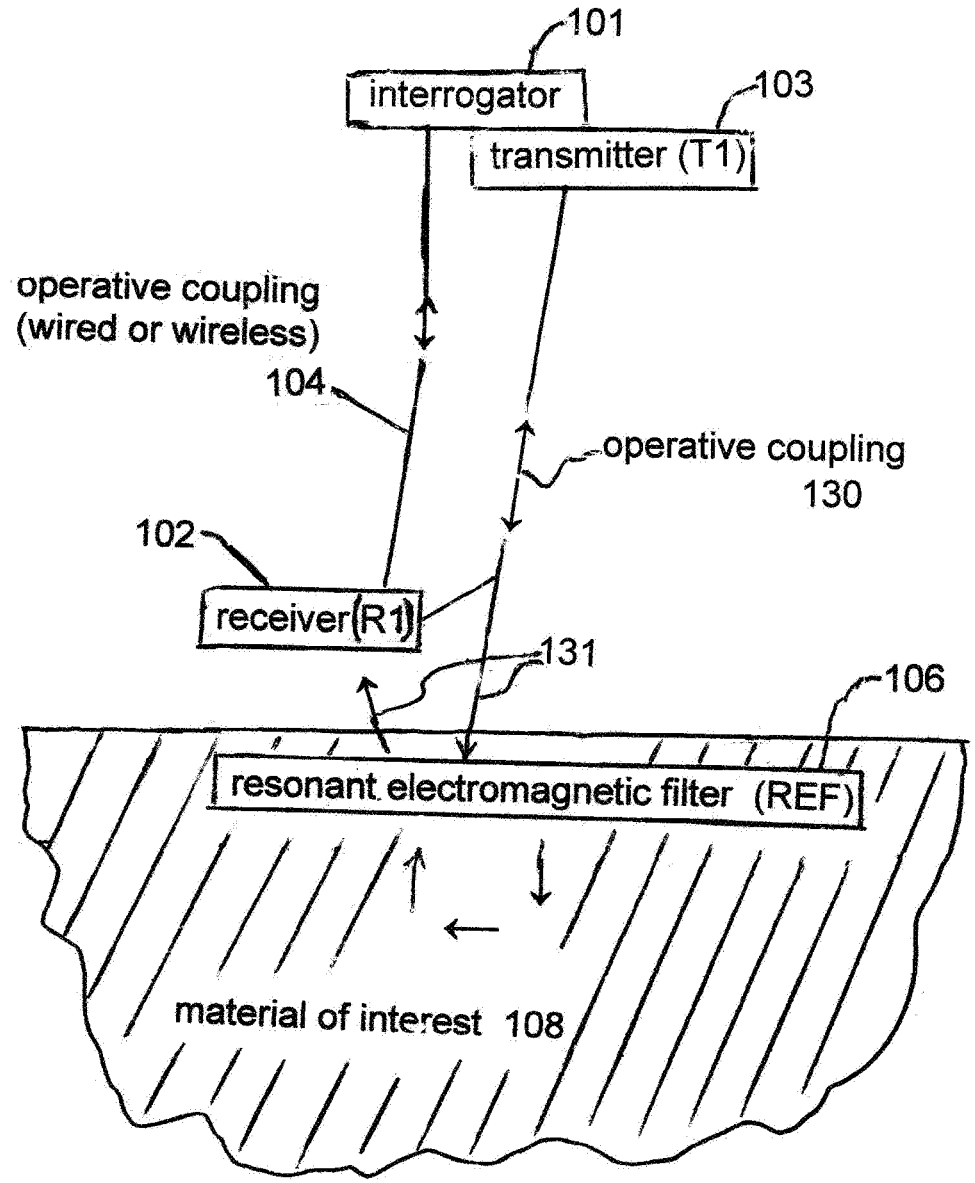
FIG. 1B depicts a second configuration in accordance with an embodiment of the invention
Figure 1C:
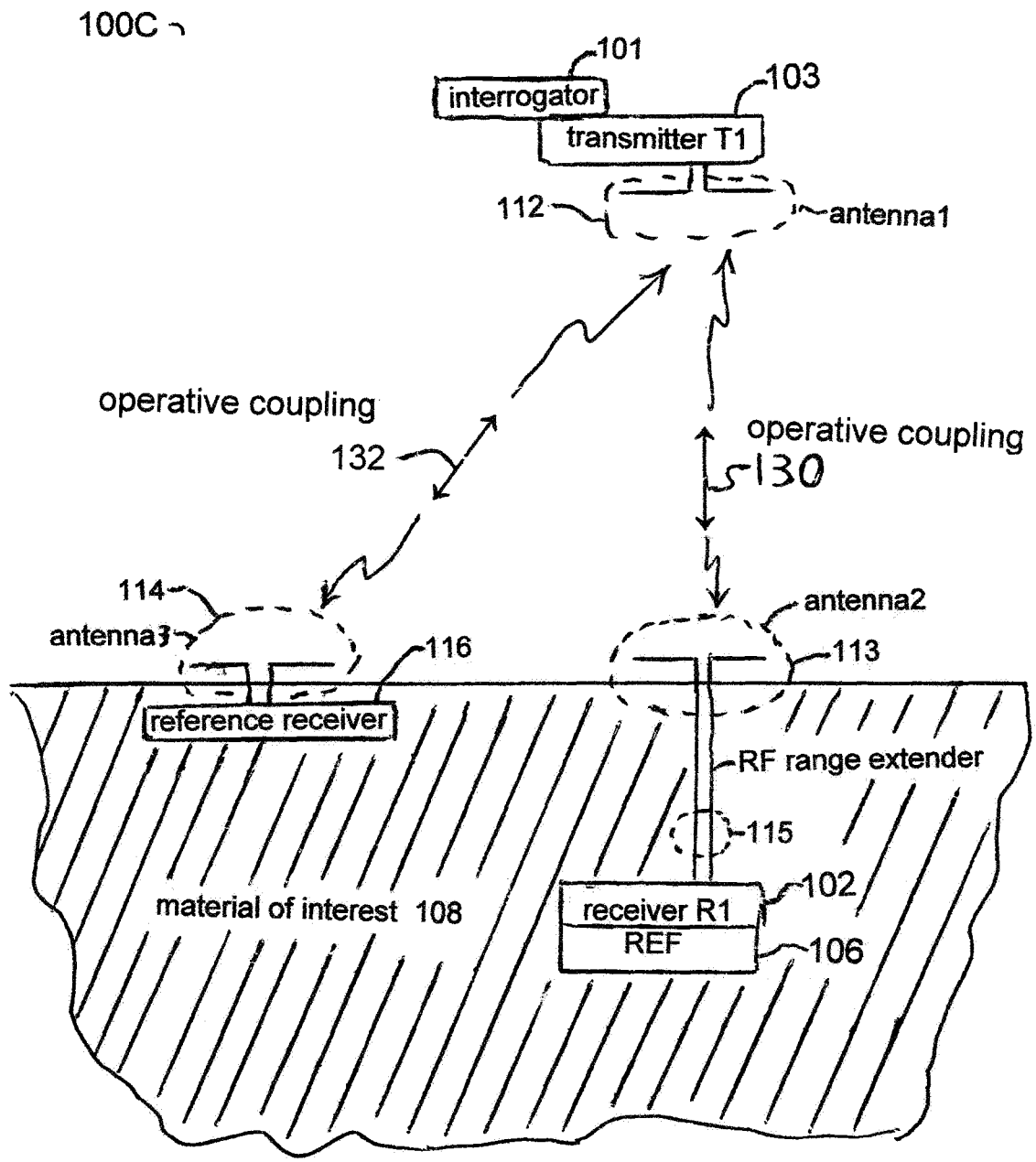
FIG. 1C depicts a third configuration in accordance with an embodiment of the invention.
Figure 2A:
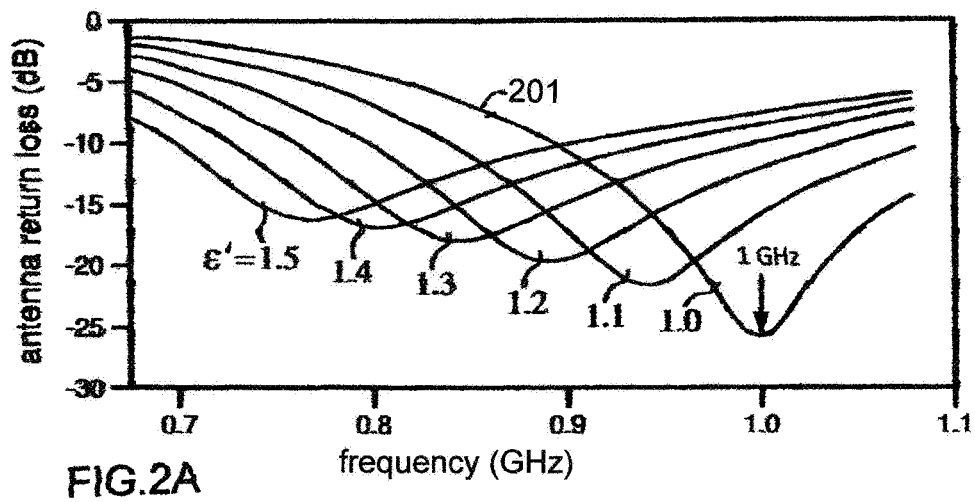
FIG. 2A is a simulation depicting response of a resonant filter affected by values of the real part of wave impedance of a surrounding material.
Figure 2B:
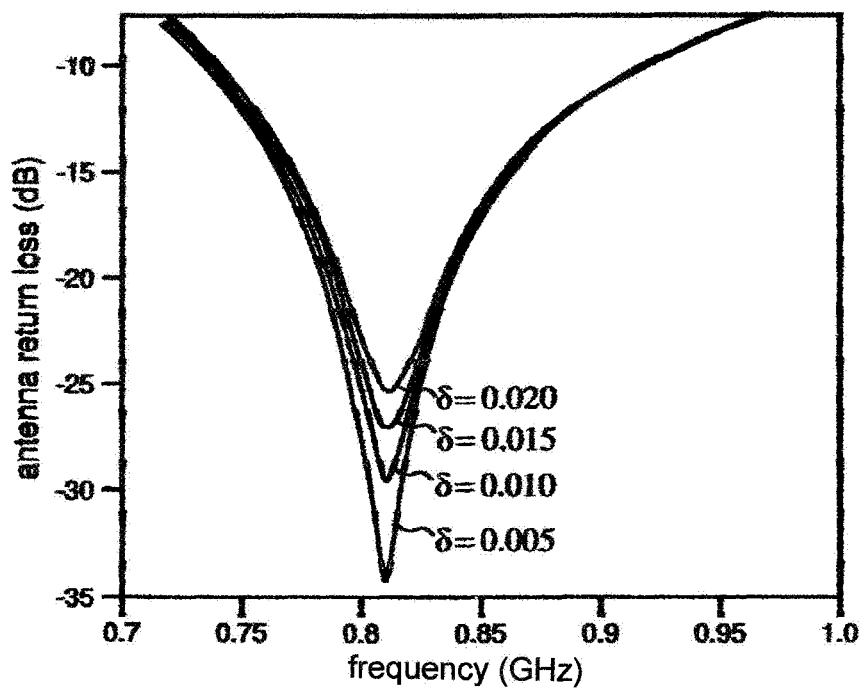
FIG. 2B is a simulation depicting response of the resonant filter affected by values of the imaginary part of wave impedance of surrounding material.
Figure 3:
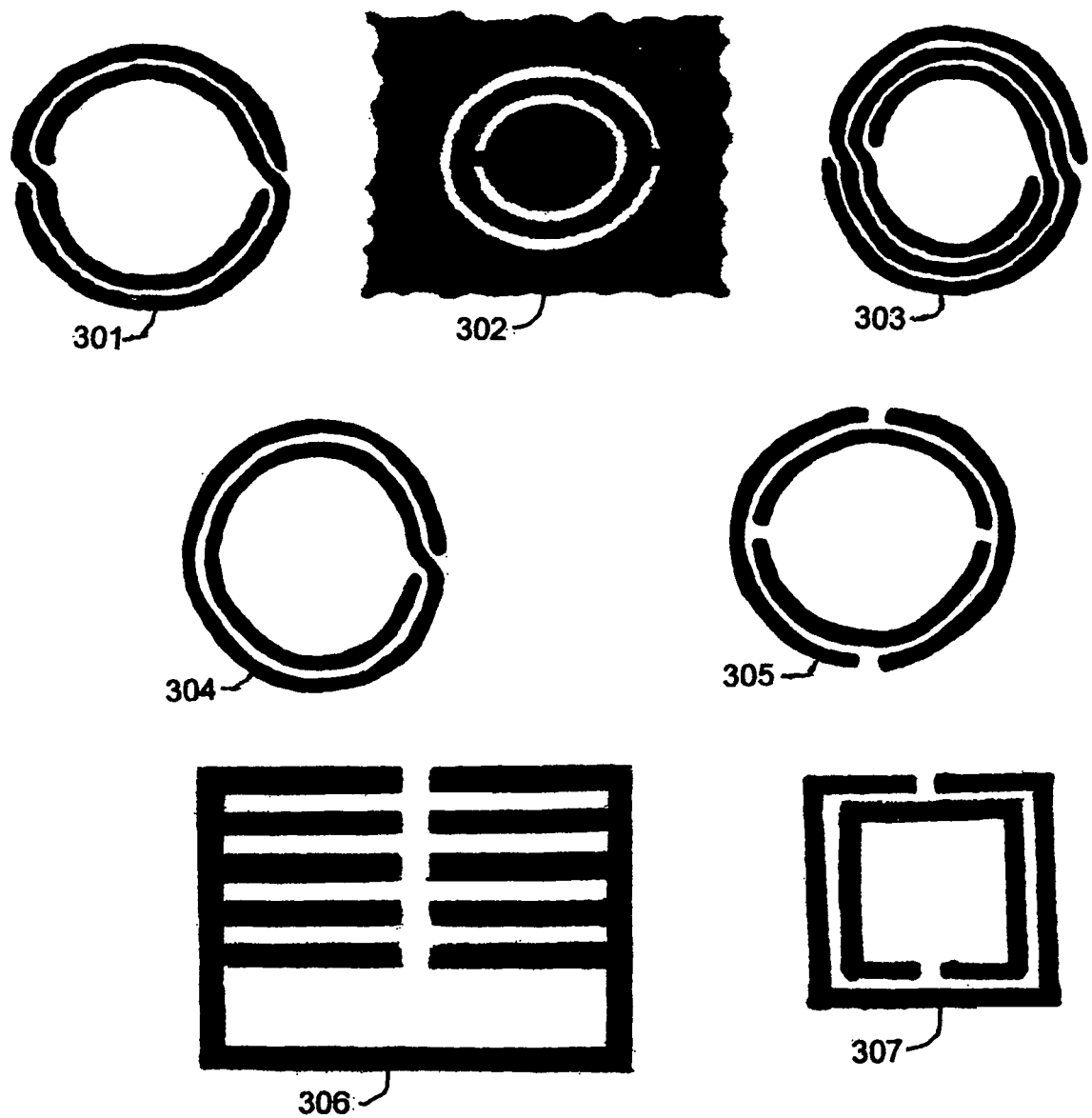
FIG. 3 depicts plan views of resonant filters comprising exemplary metamaterial resonant electromagnetic filter (MREF) structures for use in conjunction with embodiments of the invention.
Figure 10:
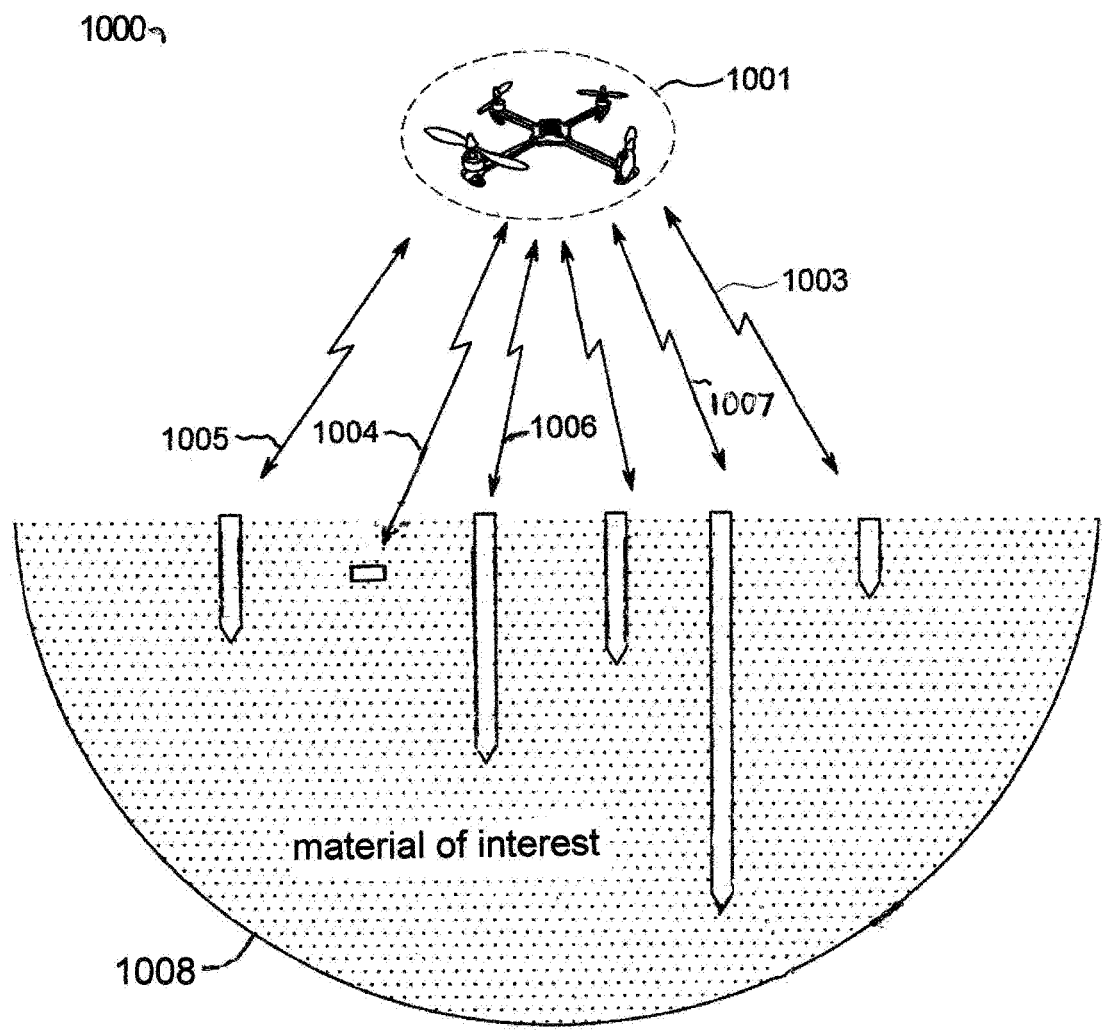
FIG. 10 depicts an embodiment of FIG. 1C programmed to receive command and control via wireless link from an interrogator carried as payload on an UAV drone in accordance with the present teachings.

FIG. 10 depicts an embodiment of FIG. 1C wherein the interrogator and transmitter T1 are disposed as payload on a UAV drone 1001. The interrogator is programmed to communicate with a plurality of receivers R1 buried in the material of interest, to control sensing operations. This configuration for the impedance spectrometer in embodiments can be configured similar to the examples of FIGS. 1B and 1C. This embodiment comprises wireless operative coupling links 1003, 1004, 2005, 1006, 1007 between the interrogator/transmitter (T1) and the respective receivers (R1). In similar embodiments, the interrogator/transmitter (T1) may be disposed in a stationary position.

It is understood that although the disclosure teaches many examples of embodiments in accordance with the present teachings, many additional variations of the invention can easily be devised by those skilled in the art after reading this disclosure. As a consequence, the scope of the present invention is to be determined by the following claims.

The invention claimed is:

1. An impedance spectrometer for sensing wave impedance of a material, the impedance spectrometer comprising an interrogator, the interrogator comprising a communication/control circuit and an impedance calculator, and a sensing structure, the sensing structure comprising a resonant electromagnetic filter (REF), an RF signal source (T1), and an RF receiver (R1), wherein:

the RF signal source (T1) couples into the material through the REF and is detected by the RF receiver (R1);

an RF response signal from the RF receiver (R1) is affected by the wave impedance of the material;

the transmitter (T1) is operatively-coupled with the interrogator by a wired and/or wireless link;

the receiver (R1) is operatively-coupled with the interrogator by a wired and/or wireless link;

the communications/control circuit provides operational control for the sensing structure and the impedance calculator, and the impedance calculator determines the real part of the wave impedance of the material based on one or more difference signal databases obtained at a frequency higher than the resonance frequency of the resonant electromagnetic filter (REF).

2. The impedance spectrometer of claim 1 wherein the impedance calculator determines the imaginary part of the wave impedance of the material based on one or more differential signal databases obtained at the at the resonance frequency of the REF.

3. The impedance spectrometer of claim 1 wherein the resonant electromagnetic filter (REF) comprises a metamaterial resonant electromagnetic filter (MREF), the MREF comprising one or more of a split ring resonator (SRR), complementary split ring resonator (CSRR), coupled spiral resonator, fractile resonator and variations/combinations thereof.

4. The impedance spectrometer of claim 1 wherein portions of the interrogator and sensing structure are disposed at one or more physical locations connected through wired and/or wireless means.

5. The impedance spectrometer of claim 1 wherein the sensing structure comprises a passive RFID sensing structure.

6. The impedance spectrometer of claim 5 wherein a wired range extender comprises operative coupling between the receiver (R1) and the interrogator.

7. The impedance spectrometer of claim 1 wherein the sensing structure comprises a strip waveguide, the strip waveguide providing signal coupling between the transmitter (T1) and the receiver (R1) and further wherein the strip waveguide is field-coupled with the resonant electromagnetic filter (REF).

8. The impedance spectrometer of claim 7 wherein the strip waveguide comprises an RF communications antenna within the operative couplings between the interrogator and the sensing structure.

9. The impedance spectrometer of claim 1 wherein the operative couplings between the interrogator and the sensing structure comprise wireless links and are operational at the same or different frequency from the RF signal source.

10. The impedance spectrometer of claim 1 wherein the sensor structure is adapted to comprise one or more transceivers, the transceivers programmed for operation as the transmitter (T1) and/or the receiver (R1).

11. The impedance spectrometer of claim 1 comprising a passive RFID sensor structure, the passive RFID sensor structure adapted to comprise a plurality of the receiver (R1) and resonant electromagnetic filter (REF) wherein the operative couplings with the interrogator and transmitter (T1) are wireless links.

12. The impedance spectrometer of claim 1 wherein the sensing structure is adapted to comprise a digital clock, the digital clock enabling operation of the impedance spectrometer at specific, programmed times and time intervals.

13. The impedance spectrometer of claim 1 wherein the transmitter (T1) and the receiver (R1) are operatively-coupled with a mobile phone through a wired databus or wireless link, the mobile phone comprising at least a portion of the interrogator.

14. The impedance spectrometer of claim 1 wherein the receiver (R1) is at least partially powered by an energy harvester, the energy harvester receiving energy from one or more of RF, solar, thermoelectric or piezoelectric energy harvesting sources.

15. The impedance spectrometer of claim 1 wherein the receiver (R1) is disposed proximal to, or within the material.

16. The impedance spectrometer of claim 1 wherein the interrogator is at least partially disposed as payload on an unmanned aerial vehicle (drone) and the sensor structure is disposed in close proximity to or disposed within the material.

17. The spectrometer of claim 1 wherein the material comprises an agricultural product, in raw or processed form, selected from a group comprised of maize, cocoa, coffee, wheat, barley, tea, nuts, peanuts, tree oils, timber, bales of hay, silage and selected plant leaf.

18. The spectrometer of claim 1 wherein the material comprises one or more of beer, wine, rum and industrial chemicals, the material further comprised of at least two components, the at least two components having a different real part of wave impedance.

19. The spectrometer of claim 1 wherein the material comprises setting cement, wherein the wave impedance of the setting cement changes with time as the cement cures.

20. A method for determining a real and/or imaginary component of a wave impedance of a material comprising a plurality of sensing operations based on calculations implemented in an impedance calculator implementing an algorithm or lookup table, a sensing operation comprising:

transmitting an RF source signal at a controlled frequency from an RF transmitter (T1), wherein the RF source signal is field-coupled through a resonant electromagnetic filter (REF) into a material receiving the RF response signal from the RF transmitter (T1) into an RF receiver (R1);

measuring a difference-signal level $\Delta V_s$ between the RF source signal and the RF response signal, wherein the difference-signal level $\Delta V_s$ is affected by the wave impedance of the material;

creating a plurality of difference signal databases comprising one or more difference signal levels $\Delta V_s$ wherein the first difference signal database is created using a material of known wave impedance and the second difference signal database is created using a material of unknown wave impedance;

a first calculation is performed in the impedance calculator using the first and second difference signal databases, wherein the controlled frequency is higher than the resonant frequency of the resonant electromagnetic filter (REF), and further wherein said first and second difference signal databases are processed with an algorithmic- or lookup-table formula to determine a real component of the wave impedance of the material;

a second calculation is performed in the impedance calculator using the first and second difference signal databases, wherein the controlled frequency is the same as the resonant frequency of the resonant electromagnetic filter (REF), and further wherein said first and second difference signal databases are processed with an algorithmic- or lookup-table formula together with the real component of the wave impedance of the material to determine both the loss tangent δ and the imaginary component of the wave impedance of the material.

* * * * *